United States Patent [19]
Hrkach et al.

[11] Patent Number: 5,654,381
[45] Date of Patent: Aug. 5, 1997

[54] FUNCTIONALIZED POLYESTER GRAFT COPOLYMERS

[75] Inventors: Jeffrey S. Hrkach, Somerville; Robert S. Langer, Newton, both of Mass.; Noah Lotan, Haifa, Israel

[73] Assignee: Massachusetts Institute of Technology, Cambridge, Mass.

[21] Appl. No.: 491,490

[22] Filed: Jun. 16, 1995

[51] Int. Cl.$^6$ .......................... C08F 283/00; C08G 63/06
[52] U.S. Cl. .......................... 525/450; 528/361; 528/363; 525/425; 525/437; 435/180; 424/418
[58] Field of Search ...................... 528/361, 363; 525/425, 437, 450; 435/180; 424/418

[56] References Cited

U.S. PATENT DOCUMENTS 5,399,665   3/1995   Barrera et al. ........................... 528/354

OTHER PUBLICATIONS

Freed, et al., "Biodegradable Polymer Scaffolds For Tissue Engineering", *Bio/Technology*, 12:689–693 (1994).
Gilding and Reed, "Biodegradable Polymers For Use In Surgery–Polyglycolic/Poly(Actic Acid) Homo–And Copolymers:1", Polymer, 20:1459–1464 (1979).
Goodman and Gilon, "Polydepsipeptides 1, Synthesis And Characterization Of Copolymers Of α–Amino And α–Hydroxy Acids", *Israel Journal Of Chem.*, 10:867–879 (1972).
Hrkach, et al., "Poly(I–lactic Acid–Co–Amino Acid) Graft Copolymers: A Class Of Functional, Biodegradable Biomaterials", Macromolecules, Chapter XX, submitted (Jun. 1995).
Imanishi, Ring–Opening Polymerization, Ivin, K.J. and Saegusa, T., Eds., Elsevier, London, 1984, vol. 2, Chapter 8.
Kricheldorf, Models Of Biopolymers By Ring–Opening Ploymerization, Penczek, S., Ed., CRC Press, Boca Raton, Chapter 1 (1990).
Kricheldorf, α–Aminoacid–N–Carboxy–Anhydrides And Related Heterocycles, Springer–Verlag, Berlin, 1987.
Langer and Vacanti, "Tissue Engineering", *Science*, 260:920–926 (1993).
Li, et al., "Structure–Property Relationship In The Case Of The Degradation Of Massive Poly(α–Hyroxy Acids) In Aqueous Media", *J. Mater. Sci. Mater. Med.*, 1:131–139 (1990).
Massia, S.P. and Hubbell, "An RGD Spacing Of 440 nm Is Sufficient For Integrin αvβ3–Mediated Fibroblast Spreading And 140 nm for Focal Contact And Stress Fiber Formation", *J.A., J. Cell. Biol.*, 114:10891100 (1991).
Mooney, et al., "Design And Fabrication Of Biodegradable Polymer Devices To Engineer Tubular Tissues", Cell Transpl., 2:203–210 (1994).
Sela, et al., "Multichain Polyamino Acids", *J. Am. Chem. Soc.*, 78:746–751 (1956).
Barrera, et al., "Synthesis And RGD Peptide Modification Of A New Biodegradable Copolymer: Poly(lactic acid–co–lysine)", *J. Am. Chem. Soc.*, 115:11010–11011 (1993).
Barrera, et al., "Copolymerization And Degradation Of Poly(lactic acid–co lysine)", Macromolecules, 28:425–432 (1995).
Daly, et al., "The Preparation Of N–Carboxyanhydrides Of α–Amino Acids Using Bis(Trichloromethyl)Carbonate", *Tetrahedron Lett.*, 29:5859–5862 (1988).

Primary Examiner—Samuel A. Acquah
Attorney, Agent, or Firm—Arnall Golden & Gregory

[57]  ABSTRACT

Synthetic, functionalized, graft copolymers of polyesters and amino acids are provided. The copolymers are formed in one embodiment by providing a linear polyester-poly(amino acid) copolymer, and reacting the amino acid groups in the linear polymer with an amino acid derivative in a polymerization reaction to form a comb-like, graft copolymer including a polyester-amino acid backbone and polyamino acid side chains extending from the amino acid groups in the backbone. The poly(amino acid) includes functional groups which permit the covalent or ionic attachment of a biological molecule to the graft copolymer. The functionalized graft copolymers can be used in a wide range of biomedical applications including tissue engineering and drug delivery.

31 Claims, No Drawings

FUNCTIONALIZED POLYESTER GRAFT COPOLYMERS

BACKGROUND OF THE INVENTION

The present invention is generally in the area of the fabrication of graft copolymers of polyesters and polyamino acids.

Poly(glycolic acid), poly(lactic acid), and their copolymers are synthetic polyesters that have been approved by the FDA for certain uses, and have been used successfully, for example, as sutures and in other biomedical applications such as drug delivery and tissue engineering for treating patients suffering from organ failure or tissue loss. Gilding and Reed, *Polymer,* 20:1459 (1979); Mooney et al., *Cell Transpl.,* 2:203 (1994); and Lewis, D. H. in *Biodegradable Polymers as Drug Delivery Systems,* Chasin, M., and Langer, R., Eds., Marcel Dekker, New York, 1990. In tissue engineering applications, isolated cells or cell clusters are attached onto synthetic biodegradable polymer scaffolds in vitro, and then the polymer-cell scaffold is implanted into recipients. Langer and Vacanti, *Science,* 260:920 (1993). Poly(glycolic acid), poly(lactic acid) and their copolymers have been used as scaffolds to support cell growth, for example of cartilage cells. Freed et al., *Bio/Technology,* 12:689 (1994). The main advantages of these materials are their degradability in the physiological environment to yield naturally occurring metabolic products, and the ability to control their rate of degradation by varying the ratio of lactic acid to glycolic acid repeat units in the copolymers.

In some tissue engineering applications, certain cells such as hepatocytes do not adhere to these polymers, however, and they cannot be used successfully as supports for cell growth. The cellular response to these polymers including adhesion and growth of cells also cannot be controlled or modified through changes in the polymer structure, because these polymers do not possess functional groups, other than end groups, that permit chemical modification to change their properties, thereby limiting the applications of these polymers.

Barrera et al. described the synthesis of a poly(lactic acid) (pLAL) copolymer consisting of L-lactic acid units and a low concentration of Nε-carbobenzoxy-L-lysine units. The polymers were chemically modified through reaction of the lysine units to introduce arginine-glycine-aspartic acid containing peptide sequences or growth factors to improve polymer-cell interactions. Barrera et al., *J. Am. Chem. Soc.,* 115:11010 (1993); and U.S. Pat. No. 5,399,665 to Bartera et al. The greatest limitation in the copolymers developed by Barrera et al. is that only a limited number of lysine units can be incorporated into the pLAL backbone. In many tissue engineering applications, the concentration of biologically active molecules attached to the polymer via the lysine groups present in the polymer would be too low to produce the desired interactions between the polymer and the body.

There is a need for the development of optimal materials for use as scaffolds to support cell growth and tissue development in tissue engineering applications. There also is a need for methods for introducing functionalities such as polyamino acids into polyesters in order to improve the biocompatibility and other properties of the polymers. There further is a need for the development of polyester materials which include a sufficient concentration of derivatizable groups to permit the chemical modification of the polymer for different biomedical applications.

It is therefore an object of the invention to provide copolymers of polyesters and polyamino acids which can be chemically modified for different biomedical applications such as tissue engineering applications. It is a further object of the invention to provide graft copolymers of polyesters and polyamino acids with improved properties such as biodegradability and biocompatibility. It is still another object of the invention to provide synthetic polyesters which can be derivatized to include functionalities such as peptide sequences or growth factors to improve the interaction of the polymer with cells.

SUMMARY OF THE INVENTION

Methods are provided for the synthesis of functionalized graft copolymers of polyesters, such as poly(glycolic acid) or poly(lactic acid), and another polymer including functionalizable groups, such as a poly(amino acid). In one embodiment, comb-like graft copolymers are provided which include a linear polyester backbone having amino acids incorporated therein, and poly(amino acid) side chains which extend from the amino acid groups in the polyester backbone. The poly(amino acid) side chains include functional groups which are capable of being chemically modified to alter the chemical or physical properties of the copolymer. For example, the functional groups may be derivatized by the attachment of a biological molecule to improve the biocompatibility or other property of the copolymer. The synthetic copolymers are useful in a variety of biomedical applications including drug delivery and tissue engineering.

DETAILED DESCRIPTION OF THE INVENTION

Biodegradable, biocompatible graft copolymers of polyesters and amino acids are provided, as well as methods for their fabrication. The graft copolymers have a comb-like structure which includes a backbone of a polyester with at least one amino acid incorporated therein, and a polymer grafted onto the amino acid which includes functional groups that are capable of being chemically modified to alter a chemical or physical property of the copolymer.

In a preferred embodiment, the comb-like graft copolymer includes a linear α-hydroxy acid polyester backbone having at least one amino acid group incorporated in the polyester, and poly(amino acid) side chains extending from the amino acid groups in the backbone. The polyesters may be polymers of α-hydroxy acids such as lactic acid, glycolic acid, hydroxybutyric acid and valeric acid, or derivatives thereof, or combinations thereof. The poly(amino acid) side chains grafted onto the polyester backbone include functional groups which permit the copolymer to be derivatized, for example, by the attachment of a molecule which alters a property of the polymer such as its compatibility with cells.

The attachment of the poly(amino acid) side chains to the polyester-backbone increases the number of accessible functional groups in the graft copolymer which can be further derivatized to alter the properties of the polymer. The number of accessible functional groups may be varied over a wide range by controlling reaction conditions in the synthesis of the graft copolymer. The graft copolymers can be adapted for use in a variety of biomedical applications by the attachment of preselected biological molecules or combinations thereof to the functional groups in the amino acid side chains in the copolymer. The graft copolymers uniquely combine the desirable properties of poly(α-hydroxy acids) such as poly(lactic acid) and poly(amino acids), and they advantageously can be designed and fabricated to promote specific, favorable interactions with the body in biomedical applications such as tissue engineering and drug delivery.

GENERAL SYNTHETIC METHODS

In one embodiment, poly(lactic acid-co-amino acid) graft copolymers are synthesized which have a polyester backbone consisting of poly(L-lactic acid-co-Z-L-lysine) (pLAL) (Formula 1).

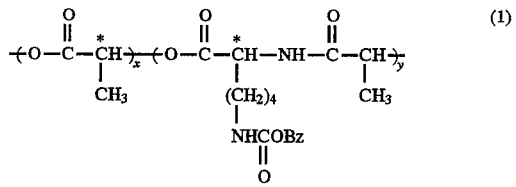

(1)

The pLAL copolymer consisting of L-lactic acid units and approximately 1–2% Nε-carbobenzoxy-L-lysine (Z-L-lysine) units is synthesized as described in Barrera et al., *J. Am. Chem. Soc.*, 115:11010 (1993). Removal of the Z protecting groups of the randomly incorporated lysine groups in the polymer chain of pLAL yields the free ε-amine which can undergo further chemical modification. Through reaction of the ε-amine group of the lysine units a variety of modifications may be made to the polymer backbone. The use of the poly(lactic acid) copolymer is advantageous since it biodegrades into lactic acid and lysine, which can be processed by the body.

To increase the amino acid content of the copolymers, the existing backbone lysine groups are used as initiating sites for the growth of poly(amino acid) side chains. The incorporation of additional amino acid groups into the polymer chain greatly increases the number of functional groups in the copolymer which are capable of being chemically modified by, for example, the attachment of a biological molecule such as a peptide.

The lysine ε-amine groups of linear poly(L-lactic acid-co-L-lysine) copolymers initiate the ring opening polymerization of an amino acid N-carboxyanhydride (NCA) to produce poly(L-lactic acid-co-amino acid) comb-like graft copolymers. In a preferred embodiment, NCAs are synthesized by reacting the appropriate amino acid with triphosgene. Daly et al., *Tetrahedron Lett.*, 29:5859 (1988). The advantage of using triphosgene over phosgene gas is that it is a solid material, and therefore, safer and easier to handle. It also is soluble in THF and hexane so any excess is efficiently separated from the NCAs.

The ring opening polymerization of amino acid N-carboxyanhydrides (NCAs) is initiated by nucleophilic initiators such as amines, alcohols, and water. The primary amine initiated ring opening polymerization of NCAs allows good control over the degree of polymerization when the monomer to initiator ratio (M/I) is less than 150. Kricheldorf, H. R. in *Models of Biopolymers by Ring-Opening Polymerization*, Penczek, S., Ed., CRC Press, Boca Raton, 1990, Chapter 1; Kricheldorf, H. R. *α-Aminoacid-N-Carboxy-Anhydrides and Related Heterocycles*, Springer-Verlag, Berlin, 1987; and Imanishi, Y. in *Ring-Opening Polymerization*, Ivin, K. J. and Saegusa, T., Eds., Elsevier, London, 1984, Volume 2, Chapter 8. Methods of using lysine ε-amine groups as polymeric initiators for NCA polymerizations are described in the art. Sela, M. et al., *J. Am. Chem. Soc.*, 78:746 (1956).

As shown in Scheme 1, in the reaction of an amino acid NCA with pLAL, the nucleophilic primary ε-amine of the lysine side chain attacks C-5 of the NCA leading to ring opening and formation of the amino acid amide, along with the evolution of $CO_2$. Propagation takes place via further attack of the amine group of the amino acid amides on subsequent NCA molecules. The degree of polymerization of the poly(amino acid) side chains, the corresponding amino acid content in the graft copolymers and their resulting physical and chemical characteristics can be controlled by changing the M/I ratio for the NCA polymerization—that is, changing the ratio of NCA to lysine ε-amine groups of pLAL.

Scheme 1

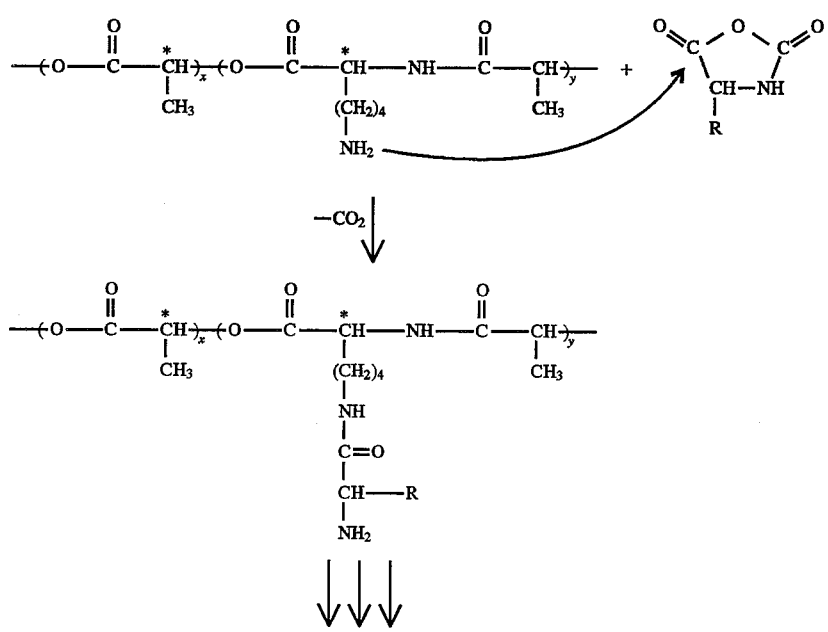

-continued
Scheme 1

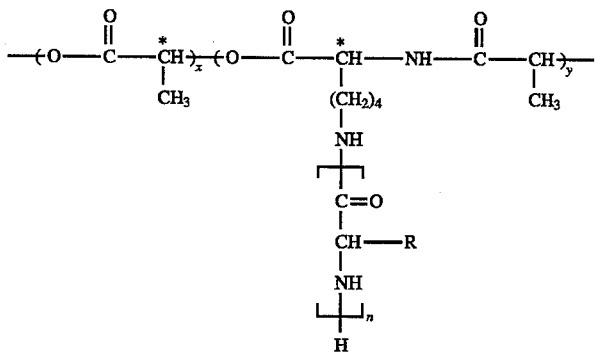

The poly(amino acid) side chains grafted onto the polyester backbone can include any amino acid, such as aspartic acid, alanine or lysine or mixtures thereof. The functional groups present in the amino acid side chains, which can be chemically modified, include amino, carboxylic acid, sulfide, guanidino, imidazole and hydroxyl groups. As used herein, the term "amino acid" includes natural and synthetic amino acids and derivatives thereof. The polymers can be prepared with a range of amino acid side chain lengths, for example, about 10–100 or more amino acids, and with an overall amino acid content of, for example, 7–72% or more depending on the reaction conditions. The grafting of poly(amino acids) from the pLAL backbone may be conducted in a solvent such as dioxane, DMF, or $CH_2Cl_2$, or mixtures thereof. In a preferred embodiment, the reaction is conducted at room temperature for about 2–4 days in dioxane.

Exemplary Graft Copolymers

Using the above method, the exemplary poly(lactic acid-co-amino acid) comb-like, graft copolymers, poly(L-lactic acid-co-Nε-carbobenzyoxy-L-lysine) (pLAL-ZLYS), poly(L-lactic acid-co-β-benzyl-L-aspartate) (pLAL-BASP), and poly(L-lactic acid-co-D,L-alanine) (pLAL-D,L-ALA), were synthesized as described in Examples 1–4. The reagents and/or other conditions such as temperature or solvent can be controlled in the reaction to vary the amino acid content in the copolymers.

Results of the reaction of pLAL with amino acid NCAs using the above procedure are presented in Table 1. The number average molecular weights ($M_n$) of pLAL used ranged from 6,000 to 50,000, providing between about 1 and 7 lysine units per pLAL backbone.

TABLE 1

Amino acid content and molecular weight of copolymers.

| Copolymer | % N[a] | Amino Acid Content (mol %) | | MW ($M_n \times 10^{-3}$) | | [NCA]$_o$/[LYS]$_o$ |
| | | actual[b] | theor.[c] | pLAL | copolymer[d] | |
| --- | --- | --- | --- | --- | --- | --- |
| pLAL | 0.40 | 1 | — | 50 | — | — |
| pLAL-ZLYS | 2.40 | 7 | 8 | 6 | 7.7 | 10 |
| | 5.39 | 22 | 17 | 50 | 100.8 | 24 |
| | 9.64 | 72 | 81 | 6 | 61.2 | 104 |
| pLAL-BASP | 0.98 | 6 | 10 | 21.2 | 24.8 | 10 |
| | 2.02 | 13 | 20 | 21.2 | 30.1 | 22 |
| | 3.97 | 35 | 50 | 50 | 119.4 | 100 |
| pLAL-D,L-ALA | 4.03 | 21 | 15 | 21.2 | 26.7 | 50 |
| | 6.91 | 35 | 38 | 50 | 77.0 | 100 |

[a]Weight % N from elemental analysis. [b]Mol % amino acid calculated from weight % N. [c]Expected amino acid content based on pLAL [LYS]$_o$ and [NCA]$_o$ assuming all NCA is polymerized and incorporated in copolymer. [d]Molecular weight of copolymer calculated from weight % N and $M_n$ pLAL.

In polymerization reactions using ZLYS-NCA and ALA-NCA, the polymerization solutions remain clear throughout, and with BASP-NCA the solutions become cloudy after 2 days, apparently due to the increasing insolubility of the pLAL-BASP copolymers as the BASP chain length increases. In each of these systems, the viscosity of the polymerization solutions increases with time as the polymerization progresses. The highest viscosity is observed in the ZLYS systems, and those producing copolymers with high lysine content become almost gel-like within 1 day. Upon completion of the reaction, GPC analysis of the precipitated graft copolymers shows only one peak, indicating that no un-reacted pLAL remains and that no linear homopoly(amino acids) are formed.

The molecular weights of the graft copolymers can be calculated using the elemental analysis data and the molecular weight of the linear pLAL used for grafting as shown for lysine from the following equations:

$$MW \text{ graft copolymer} = M_n \text{ pLAL} + MW \text{ pZLYS} \quad (1)$$

where $M_n$ pLAL is the number average molecular weight of pLAL determined by GPC and MW pZLYS is the molecular weight of the pZLYS chains calculated from. Equation (2):

$$MW\,pZLYS = \frac{M_n\,pLAL}{\frac{2800}{262\,x} - 1} \qquad (2)$$

where x is the value of % N obtained from elemental analysis.

As an example, the MW of the graft copolymer can be calculated for a graft copolymer with 72% Z-lysine content. The corresponding % N from elemental analysis is 9.64 and $M_n$ pLAL determined by GPC is 5,500. Therefore, from Equation (2), the MW of the pZLYS chains is 50,640, and the MW of the graft copolymer from Equation (1) is equal to 56,140.

Table 1 includes the mol %N from elemental analysis and the actual amino acid content of the polymers based on the % N. Table 1 also includes the theoretical amino acid mol % which is calculated based on the initial concentration of lysine groups present in the pLAL chains (pLAL[LYS]$_o$) and the initial concentration of NCA ([NCA]$_o$) assuming that all of the NCA is polymerized and incorporated into the polymer. Table 1 further includes the ratio of pLAL[LYS] and NCA used in the reaction. As illustrated in Table 1, the degree of polymerization of the poly(amino acid) side chains and the corresponding amino acid content in the graft copolymers can be controlled by changing the M/I ratio for the NCA polymerization—that is, changing the ratio of NCA to lysine ε-amine groups of pLAL.

Poly(L-lactic acid-co-L-lysine)

The poly(L-lactic acid-co-Z-L-lysine) graft copolymers (pLAL-ZLYS) listed in Table 1 were synthesized from pLAL and ZLYS-NCA as described in Example 2, with lysine contents ranging from about 7-72 mol %. The molecular weight of the graft copolymers varies depending upon the initial molecular weight of pLAL, the number of lysine groups present in each pLAL chain, the concentration of Z-L-lysine N-carboxyanhydride (ZLYS-NCA) used in the reaction, and the amount of amino acid incorporated. Poly (Z-L-lysine) degrees of polymerization, for example, ranging from approximately 10 to 100 amino acid units are present in each grafted poly(amino acid) chain.

The solubilities of the lysine graft copolymers differ from that of pLAL. PLAL is soluble in less polar solvents such as $CHCl_3$ and $CH_2Cl_2$, whereas the graft copolymers are only soluble in more polar solvents such as DMF, DMSO, and hexafluoroisopropanol (HFIP). The range of the lysine content (i.e. the number of reactive sites) in these copolymers that can be attached to the copolymers is 35 times greater than the previously synthesized pLAL of Barrera et al. containing only 2% lysine in the polymer backbone. The increase in the lysine content greatly increases the amount of amino functional groups in the polymer which permits, for example, a higher density of biological molecules to be attached for use in a particular application such as tissue engineering. The number of reactive lysine sites can be varied over a broad range in a well controlled manner.

After removal of the Z protecting group, poly(L-lactic acid-co-L-lysine) graft copolymers with free amines are obtained which can be used for the attachment of biologically active molecules. Additionally, in neutral solution, the amine groups are protonated, and therefore can bind negatively charged molecules including polynucleotides such as DNA, polysaccharides and heparin. Thus these copolymers can be readily derivatized for different biomedical applications.

Poly(L-lactic acid-co-β-benzyl-L-aspartate)

Poly(L-lactic acid-co-β-benzyl-L-aspartate) (pLAL-BASP) graft copolymers with BASP contents in the rage of 6-35 mol % listed in Table 1 were synthesized as described above and in Example 3 from pLAL and BASP-NCA. Precipitation of poly(L-lactic acid-co-β-benzyl-L-aspartate) graft copolymers during the synthesis reduces the BASP content in the copolymers in comparison to the yield calculated from the ratio of BASP-NCA to lysine ε-amine groups of pLAL (the M/I ratio for the NCA polymerization) due to the insolubility of the product. However, suitable solvents and solvent mixtures could readily be selected to improve the yield for applications where a higher BASP content in the polymer is needed. Removal of the benzyl protecting groups of BASP to produce aspartic acid groups provides free carboxylic acid groups in the copolymer which may be further derivatized.

PLAL-ASP films were cast from HFIP and analyzed by ESCA to determine the level of nitrogen at the surface (top 100 Å) of the films, as described in Example 3. The amount of nitrogen at the surface of the films is important in tissue engineering applications, since it relates directly to the amount of cell adhesion peptides that will be available to interact with cells when seeded onto the modified polymers. In the case of pLAL, which had only 2 mol % lysine, no nitrogen was detected when films were analyzed by ESCA. In contrast, for a film of pLAL-ASP containing 19 mol % ASP in the copolymer, the amount of ASP at the surface of the film was calculated to be approximately 15% using the integration of the area of the nitrogen peak relative to the other peaks in the ESCA spectrum.

This illustrates the presence and availability of free amino acids containing carboxyl groups on the surface of the copolymer. The carboxylic groups can be utilized for the attachment of biologically active molecules, such as RGD peptides. In addition, in a neutral aqueous environment, the poly(aspartic acid) side chains will be deprotonated, offering a negatively charged environment, which can allow the ionic attachment of positively charged molecules.

Poly(L-lactic acid-co-D,L-alanine) Poly(L-lactic acid-co-D,L-alanine) (pLAL-ALA) graft copolymers were prepared from pLAL and D,L-ALA-NCA as described above and in Example 4. Although it is not charged, poly (D,L-alanine) is a water soluble poly(amino acid), since the racemic mixture does not allow the formation of an internally hydrogen-bonded secondary structure that will prevent its solubility. As a result, the pLAL-ALA copolymers are more hydrophilic than poly(lactic acid). This can be advantageous for applications where a hydrophilic material is required, yet a strongly charged environment cannot be tolerated. In addition, the ALA chains possess a terminal amine group that can be utilized for the attachment of biologically active molecules.

The reaction was conducted in dioxane, and the solution remained clear throughout the polymerization. In contrast, poly(ALA) formed in the homopolymerization of ALA-NCA initiated by n-butyl amine under the same conditions precipitated out of the polymerization solution. Therefore, the pLAL keeps the polyALA chains soluble in dioxane. This is significant, since this illustrates that one can not only modify the properties of poly(lactic acid) in the synthesis of the pLAL-amino acid graft copolymers, but also the properties of poly(amino acids).

Biomedical Applications

Polyester graft copolymers are provided which may be used in a variety of biomedical applications, such as the fabrication of materials for use as sutures, artificial hearts and blood vessels, controlled release drug delivery systems, and supports for cell growth in tissue engineering. Biodegradable, biocompatible linear polyesters can be modified as described herein to form graft copolymers suitable for a particular biomedical application. The graft copolymers possess a higher density of functional groups than linear polyester-poly(amino acid) copolymers, and therefore may be much more readily modified chemically to alter theft properties. Copolymers may be fabricated such that the response within the body to their presence is minimized, and wherein specific, favorable interactions between the polymers and the body are promoted.

In one embodiment, comb-like graft copolymers including a polyester backbone, such as poly(lactic acid), having at least one amino acid incorporated therein, and a poly (amino acid) extending from the amino acid in the polyester backbone are fabricated as discussed herein. The incorporation of selected amino acid chains into the poly(lactic acid) structure can introduce new properties, such as improved biocompatibility, into poly(lactic acid) based materials, without losing the beneficial properties of poly(lactic acid) such as biodegradability and low toxicity. The properties of the polymer and the resulting biomedical use of the polymer will depend upon the particular amino acid used as well as the poly(amino acid) chain length and overall structure of the copolymer.

The poly(amino acid) side chains in the graft copolymers possess functional groups which can be used as sites for further chemical modification to alter a chemical or physical property of the graft copolymer. The polymers may be chemically modified in order to tailor the resulting biomaterials for a particular biomedical application by, for example, the ionic or covalent attachment of a biological molecule to the functional groups on the poly(amino acid) side chains, using standard chemical techniques available in the art and described for example in U.S. Pat. No. 5,339,665, the disclosure of which is incorporated herein by reference. As used herein, the term "biological molecule" includes natural and synthetic molecules which can alter a physical or chemical property of the copolymer to which it is attached, such as specific binding properties, hydrophilicity, or bioactivity. Exemplary biological molecules include amino acids, saccharides, nucleic acids, lipids, and polymers and mixtures thereof. For example, biological molecules such as peptides, proteins, growth factors, drugs, and antibodies may be utilized.

Tissue Engineering

In one embodiment, graft copolymers may be derivatized for use in tissue engineering applications by the attachment of biologically active molecules to the functional groups on the poly(amino acid) side chains that promote favorable cell-polymer interactions, such as cell adhesion molecules and growth factors. In these applications, a matrix of the modified graft copolymers is seeded with cells, implanted into an animal, and used as a scaffold for cell growth. These materials can be tailored to fit the particular needs of a variety of cell types through changes in the type and level of cell adhesion peptides attached to the copolymers. Cell types which can be seeded on the matrices include hepatocytes, uroendothelial cells, skin cells, muscle cells, nerve cells and bone cells.

For example, peptides possessing an RGD (arginine-glycine-aspartic acid) amino acid sequence may be attached to the graft copolymers. The RGD sequence, present in proteins such as fibronectin, has been shown to be active in promoting cell adhesion and growth. Massia, S. P. and Hubbell, J. A., *J. Cell. Biol.*, 114:1089 (1991). Incorporation of RGD sequences as part of the copolymer structure thus can enhance cell growth. This can be useful in some cases for tissue engineering, wherein polyesters to which cells such as hepatocytes do not normally adhere can be modified to enable them to be used successfully as supports for cell growth. Additionally, biologically active molecules may be incorporated into the copolymer which promote the adhesion and growth of a particular cell type in vivo.

Drug Delivery

The graft copolymers also may be formed into matrices for use as drug delivery systems. In this application, a drug, such as a bioactive peptide, protein, growth factor, antibody, polynucleic acid, organic compound, or metal may be attached to the functional groups on the poly(amino acid) side chain of the graft copolymer using methods available in the art. The copolymers may be modified to increase the level of the drug agent incorporated. Agents which provide greater stability for the drug's delivery may be covalently or ionically attached to the copolymer. In addition, the copolymers may be functionalized with a specific binding moiety, e.g., an antibody, which targets the polymer for delivery to a particular site within the body. Hydrophilic, hydrophobic, acidic, basic or ionic groups also may be attached to the copolymers to expand their use as delivery devices for hydrophilic drugs. Matrices of the modified drug-containing graft copolymer may be administered to an animal orally or parenterally to deliver the drug to the animal in vivo at a site in the animal where it is needed.

Other Applications

The degradation of linear poly(lactic acid) and poly (glycolic acid) polymers into lactic or glycolic acid can lead to a highly acidic local environment which can have a detrimental effect on the agents being delivered. Li et al., *J. Mater. Sci. Mater. Med.*, 1:131 (1990). This can be avoided by the incorporation of basic functionalities into the graft copolymers that can neutralize the acids and control the pH.

The present invention will be further understood by references to the following non-limiting examples, in which the following materials and equipment were utilized.

Materials

THF and dioxane were distilled from sodium and stored over sodium-potassium alloy in the dry box. $CH_2Cl_2$ and $CHCl_3$ were refluxed over $CaH_2$, and then distilled onto and stored over $CaH_2$. DMF was stirred overnight over KOH, then distilled from $CaO_2$. All other solvents were used as received. Nε-Carbobenzoxy-L-lysine (ZLYS), b-benzyl-L-aspartate (BASP), and D,L-alanine (ALA) (all from Sigma) and triphosgene (Aldrich) were stored in the freezer in the dry box and used as received. HBr (Aldrich, 30 wt % in acetic acid) was used as received. N,N-Diisopropylethyl amine (Aldrich) was stored over molecular sieves, or distilled from $CaH_2$.

Equipment

Reactions were set up or run in a Vacuum Atmospheres dry box (model HE-43-2). All copolymers were analyzed after precipitation, isolation, and drying under vacuum at room temperature. NMR spectra were collected on a Braker AC250 FTNMR in $CDCl_3$, $d_7$-DMF, or $d_6$-DMSO. GPC analysis was conducted in DMF (Phenogel linear column; Phenomenex) or $CHCl_3$ (Phenogel guard, linear, and 1000 Å columns in series; Phenomenex) using a Perkin Elmer model 250 pump and model LC30 differential refractive index detector. IR spectra were collected on a Nicolet 550 FTIR as KBr pellets. Electron Spectroscopy for Chemical Analysis (ESCA) was carried out on a Perkin Elmer Model 5100 X-ray Photoelectron Spectrometer. Molecular weights of pLAZL and pLAL were calculated based on polystyrene standards (PolySciences). Elemental analyses were performed by Quantitative Technologies, Inc., Whitehouse, N.J.

EXAMPLE 1: Synthesis of poly(L-lactic acid-co-amino acid) graft copolymers.

Amino acid N-carboxyanhydrides (NCAs) were synthesized using the procedure reported by Daly. Daly et al.,

*Tetrahedron Lett.*, 29:5859 (1988). Three equivalents of triphosgene in THF were added to the stirred suspension of amino acid in THF at 60° C. A clear solution is obtained within 1 hour. After 3 hours, excess hexane was slowly added to precipitate the NCA. The mixture was stored overnight in a freezer (−30° C.) in a dry box, and vacuum filtered to produce the NCAs. The NCAs of ZLYS (N$\epsilon$-carbobenzoxy lysine), BASP and ALA were prepared by this procedure. Although they are sensitive materials, the amino acid NCA's can be stored in a freezer (−30° C.) in the dry box and used effectively after several days.

Poly(L-lactic acid-co-Z-L-lysine) (pLAZL), a linear copolymer containing approximately 1 mol % lysine in the backbone, was synthesized as previously described by Barrera et al. Barrera et at., *J. Am. Chem. Soc.*, 115:11010 (1993). PLAZL was deprotected to yield poly(L-lactic acid-co-L-lysine) (pLAL) by first dissolving it in $CHCl_3$, then adding HBr/HOAc (10–15 fold excess of polymer) and stirring under argon for 30–60 min. The polymer was precipitated with ether, washed with methanol and collected by vacuum filtration. Conversion from the hydrobromide salt to the free amine was carried out in $CHCl_3$ by reaction with excess diisopropylethyl amine. Precipitation from methanol and drying yielded pLAL with free $\epsilon$-amine groups. Analysis of the polymer by $^1H$ NMR shows the disappearance of the Z-phenyl peak at 7.35 ppm to indicate deprotection was complete.

The reaction of pLAL with amino acid NCAs or mixtures thereof to produce the poly(L-lactic acid-co-amino acid) graft copolymer then is conducted using the appropriate amino acid NCAs using the procedure described in Example 2 for the synthesis of poly(L-lactic acid-co-Z-L-lysine) graft copolymers.

Example 2: Synthesis of poly(L-lactic acid-co-Z-L-lysine) graft copolymers.

ZLYS-NCA and pLAL were prepared as described in Example 1. In one run, in a dry box, pLAL (1 g, 0.14 mmol lysine) was dissolved in 10 mL dioxane, and then a dioxane solution of ZLYS-NCA (1.02 g in 5 mL dioxane, 3.33 mmol) was added. The graft copolymerization mixture was brought out of the dry box, purged with argon throughout the reaction or equipped with a drierite drying tube, and stirred at room temperature for 2–4 days. The graft copolymer, was precipitated by slowly adding a large excess of methanol, vacuum filtered, and dried under vacuum on a lyophilizer, obtaining a yield of 1.5 g (80%). The copolymers obtained by this method were analyzed by elemental analysis (see Table 1) as well as $^1H$ NMR and IR.

The $^1H$ NMR spectrum of pLAL includes a peak of the methine proton of the lactic acid repeat units at 5.15 ppm which is much larger than the phenyl peak of the Z protecting group of the lysine units at 7.35 ppm. The NMR spectrum of a pLAL-ZLYS graft copolymer in $d_7$-DMF with increased lysine content (e.g., 7%) has a much larger phenyl peak. Additionally, due to the increased lysine content in the polymer, the benzyl $CH_2$ peak of the Z protecting group is visible at 4.9 ppm.

Removal of the Z groups from pLAL-ZLYS was effected using HBr/HOAc in a method similar to that used to deprotect the pLAZL linear copolymers described in Example 1. $^1H$ NMR analysis of the resulting copolymer shows no Z phenyl peak indicated that complete deprotection was achieved. At this stage, the $\epsilon$-amines of the lysine units of the copolymer are in the form of the hydrobromide salts. Further reaction with diisopropylethyl amine yields the free amines, which can be used as reactive sites for the attachment of biologically active molecules.

The graft copolymers were analyzed by infrared spectroscopy as KBr pellets. The IR spectrum of poly(L-lactic acid) includes an ester peak at 1759 $cm^{-1}$ and aliphatic peaks at 2999 $cm^{-1}$ and 2964 $cm^{-1}$. The IR spectrum of a pLAL-ZLYS graft copolymer with 7% lysine content shows new peaks at 3303 $cm^1$, 1653 $cm^{-1}$ (amide I) and 1531 $cm^{-1}$ (amide II) corresponding to the poly(Z-L-lysine) backbone, and at 1700 $cm^{-1}$ from the carbamate peaks of the Z protecting group. These peaks are proportionally stronger in the IR spectrum of a pLAL-ZLYS graft copolymer with 72% lysine content.

Example 3: Synthesis of poly(L-lactic acid-co-L-aspartic acid) graft copolymers

BASP-NCA and pLAL were prepared as generally described in Example 1. PLAL-BASP graft copolymers were prepared from pLAL and BASP-NAC by the procedure generally described in Example 2.

Deprotection of PLAL-BASP was implemented as follows, under dry conditions to prevent the hydrolysis of the ester bonds of the poly(lactic acid) backbone of pLAL-BASP. A fine powder of pLAL-BASP with 20% BASP content (700 mg, 7.1 mmol polymer, 1.42 mmol BASP) is added to an oven dried (cooled under argon) 50 mL round bottom flask equipped with a stir bar. To this, 20 mL HBr/HOAc is added via syringe. The mixture is allowed to stir under argon for 14–20 h, then is transferred to a beaker. Ether (100 mL) is added to the mixture to dilute the acid and precipitate the polymer. At this point, the polymer is yellow and sticky due to excess HBr. Successive washings (typically 3) with ether and then methanol (typically 2) yield a powdery, off-white precipitate. The precipitate is collected and dried under vacuum at room temperature. The yield is approximately 85 mol %.

The poly(L-lactic acid-co-$\beta$-benzyl-L-aspartate) (pLAL-BASP) graft copolymers were analyzed by $^1H$ NMR. Characteristic peaks observed in the spectrum included: peaks for the benzyl protecting groups of the BASP repeat units at 7.4 ppm and 5.1 ppm; small, broad peaks at 8.3 ppm and 4.7 ppm corresponding to the NH and $\alpha$-CH, respectively, in the BASP backbone; and a quartet of the methine peak of the lactic acid repeat units at 5.3 ppm; a methyl peak at 1.5 ppm; and the BASP $CH_2$ peak at 2.8 ppm. The NMR spectrum of the polymer after treatment with HBr to form pLAL-ASP in $d_6$-DMSO also was obtained. The disappearance of the benzyl peaks at 7.3 ppm and 5.1 ppm was observed, indicating that complete deprotection had occurred. GPC analysis indicated that no degradation occurred during deprotection.

PLAL-ASP films were cast from hexafluoroisopropanol (HFIP) onto glass or aluminum surfaces. Aluminum was used for the casting of samples for ESCA due to ease of sample preparation. Film thicknesses vary depending upon pLAL-ASP concentration. Casting 50 mg pLAL-BASP in 0.5 mL HFIP onto an aluminum surface with an area of approximately 16 $cm^2$ yielded a film with a thickness of approximately 65±5 μm as measured by a micrometer.

PLAL-ASP films cast from HFIP were analyzed by ESCA (electron spectoscropy for chemical analysis) to determine the level of nitrogen at the surface (top 100 Å) of the films. In the case of pLAL, which had only 2 mol % lysine, no nitrogen was detected when films were analyzed by ESCA. However, a nitrogen peak was present for a film of pLAL-ASP containing 19 mol % ASP in the copolymer. The amount of ASP at the surface of the film was calculated to be approximately 15% by using the integration of the area of the nitrogen peak relative to the other peaks in the ESCA spectrum.

Example 4: Synthesis of poly(L-lactic acid-co-D,L-alanine) graft copolymers.

ALA-NCA and pLAL were prepared as described in Example 1. Poly(L-lactic acid-co-D,L-alanine) (PLAL-ALA) graft copolymers were prepared from pLAL and ALA-NAC by the procedure generally as described in Example 2.

PLAL-ALA graft copolymers with a 21% ALA content as well as a 35% ALA content were prepared as shown in Table 1. The $^1$H NMR spectrum of PLAL-ALA was obtained and included: broad NH and CH peaks of the ALA backbone at 7.95 ppm and 4.2 ppm, respectively; the quartet of the methine peak of the lactic acid repeat units at 5.2 ppm; and the methyl peaks for the lactic acid repeat units and ALA at 1.45 ppm and 1.2 ppm, respectively.

Modifications and variations of the present invention will be obvious to those skilled in the art from the foregoing detailed description. Such modifications and variations are intended to come within the scope of the following claims.

What is claimed is:

1. A biocompatible, graft copolymer formed by:

reacting a linear α-hydroxy-acid polyester copolymer having at least one amino acid group incorporated therein and monomeric amino acid derivatives, to form a graft copolymer comprising a polyester copolymer and at least one poly(amino acid) side chain extending from an amino acid group in the polyester copolymer;

wherein the poly(amino acid) side chain includes at least one amino acid which comprises an ionically or covalently modifiable functional group.

2. The graft copolymer of claim 1 wherein the polyester copolymer comprises an α-hydroxy acid selected from the group consisting of lactic acid, glycolic acid, hydroxybutyric acid and valeric acid, and mixtures thereof.

3. The graft copolymer of claim 1 wherein the linear α-hydroxy-acid polyester copolymer comprises a poly(lactic acid) polymer having at least one lysine group incorporated therein; and wherein the poly(amino acid) extends from at least one lysine group in the polyester copolymer.

4. The graft copolymer of claim 3 wherein the poly(amino acid) is a polymer of an amino acid selected from the group consisting of aspartic acid, lysine and alanine, and mixtures thereof.

5. The graft copolymer of claim 3 selected from the group consisting of a poly(L-lactic acid-co-L-lysine), a poly(L-lactic acid-co-β-benzyl-L-aspartate), and a poly(L-lactic acid-co-D,L-alanine) graft copolymer.

6. The graft copolymer of claim 3 wherein the poly(amino acid) side chain includes between about 10 and 100 amino acids.

7. The graft copolymer of claim 3 having an amino acid content of between about 7 and 72%.

8. The graft copolymer of claim 1 wherein the functional group is covalently or ionically attached to a biological molecule.

9. The graft copolymer of claim 8 wherein the biological molecule is selected from the group consisting of a cell adhesion molecule, a growth factor, a drug, an antibody, a peptide and a protein.

10. The graft copolymer of claim 8 wherein the biological molecule includes a functional group selected from the group consisting of a hydrophilic group, a hydrophobic group, an acidic group, a basic group and an ionic group.

11. The graft copolymer of claim 8 wherein the modifiable functional group is selected from the group consisting of amino, carboxylic acid, sulfide, guanidino, imidazole and hydroxyl groups.

12. The graft copolymer of claim 8 wherein the modifiable functional group is a protonated amine ionically attached to the biological molecule; and wherein the biological molecule is selected from the group consisting of a polynucleotide and a polysaccharide.

13. A method of forming a biocompatible graft copolymer, the method comprising:

reacting a linear α-hydroxy-acid polyester copolymer, having at least one amino acid incorporated therein, in a polymerization reaction with monomeric amino acid derivatives thereby to form a graft copolymer comprising the polyester copolymer with a poly(amino acid) side chain extending from an amino acid group in the polyester copolymer;

wherein the poly(amino acid) side chain includes at least one amino acid which comprises an ionically or covalently modifiable functional group.

14. The matrix of claim 13 wherein at least a portion of the functional groups are covalently or ionically attached to an agent which promotes the stability of the drug.

15. The method of claim 13 wherein the method further includes covalently or ionically attaching a biological molecule to the functional group.

16. A method of improving the biocompatibility properties of a linear α-hydroxy-acid polyester backbone having at least one amino acid group incorporated therein, the method comprising:

reacting the polyester with an amino acid derivative thereby to form a poly(amino acid) polymer extending from an amino acid group in the polyester backbone;

wherein the poly(amino acid) includes functional groups capable of altering a chemical or physical property of the polyester.

17. The method of claim 13 wherein the poly(amino acid) side chain includes between about 10 and 100 amino acids.

18. The method of claim 13 wherein the graft copolymer has an amino acid content of between about 7 and 72%.

19. The method of claim 13 wherein the polyester copolymer comprises an α-hydroxy acid selected from the group consisting of lactic acid, glycolic acid, hydroxybutyric acid and valeric acid, and mixtures thereof.

20. The method of claim 14 wherein the polyester copolymer comprises a poly(lactic acid) polymer having at least one lysine group incorporated therein; and wherein the amino acid derivative is lysine N-carboxyanhydride which is reacted with the polyester copolymer to produce a poly(lysine) side chain extending from at least one lysine group in the polyester copolymer.

21. The method of claim 14 wherein the amino acid is selected from the group consisting of aspartic acid, lysine, alanine, and mixtures thereof.

22. The method of claim 13 wherein the graft copolymer is selected from the group consisting of a poly(L-lactic acid-co-L-lysine), a poly(L-lactic acid-co-β-benzyl-L-aspartate), and a poly(L-lactic acid-co-D,L-alanine) graft copolymer.

23. The method of claim 15 wherein the biological molecule is selected from the group consisting of a peptide and a protein.

24. The method of claim 15 wherein the biological molecule includes a functional group selected from the group consisting of a hydrophilic group, a hydrophobic group, an acidic group, a basic group and an ionic group.

25. The method of claim 13 wherein the functional group is selected from the group consisting of amino, carboxylic acid, sulfide, guanidino, imidazole and hydroxyl groups.

26. The method of claim 15 wherein the modifiable functional group is a protonated amine ionically attached to the biological molecule; and wherein the biological molecule is selected from the group consisting of a polynucleotide and a polysaccharide.

27. The method of claim 15 wherein the modifiable functional group is a protonated amine ionically attached to the biological molecule; and wherein the biological molecule is heparin.

28. The method of claim 15 wherein the biological molecule alters a chemical or physical property of the graft copolymer.

29. The graft copolymer of claim 8 wherein the modifiable functional group is a protonated amine ionically attached to the biological molecule; and wherein the biological molecule is heparin.

30. The graft copolymer of claim 8 wherein the biological molecule alters a chemical or physical property of the graft copolymer.

31. The graft copolymer of claim 1 wherein the graft copolymer is biodegradable.

* * * * *

UNITED STATES PATENT AND TRADEMARK OFFICE
CERTIFICATE OF CORRECTION

PATENT NO. : 5,654,381
DATED : August 5, 1997
INVENTOR(S) : Jeffrey S. Hrkach, Robert S. Langer, and Noah Lotan It is certified that error appears in the above-indentified patent and that said Letters Patent is hereby corrected as shown below:

Column 1, before line 5, insert

--This invention was made with government support under Grant No. BCS9202311 awarded by the National Science Foundation. The government has certain rights in the invention.--

Signed and Sealed this

Sixteenth Day of December, 1997

Attest:

BRUCE LEHMAN

Attesting Officer

Commissioner of Patents and Trademarks